United States Patent [19]

De Felippis

[11] Patent Number: 5,461,031
[45] Date of Patent: Oct. 24, 1995

[54] MONOMERIC INSULIN ANALOG FORMULATIONS

[75] Inventor: Michael R. De Felippis, Indianapolis, Ind.

[73] Assignee: Eli Lilly and Company, Indianapolis, Ind.

[21] Appl. No.: 260,633

[22] Filed: Jun. 16, 1994

[51] Int. Cl.$^6$ .......................... A61K 38/28; C07K 14/62
[52] U.S. Cl. ................................. 514/4; 514/3; 530/304
[58] Field of Search ............................... 530/304; 514/3, 514/4

[56] References Cited

U.S. PATENT DOCUMENTS

| | | | |
|---|---|---|---|
| 2,538,018 | 1/1951 | Krayenbühl et al. | 167/75 |
| 2,801,953 | 8/1957 | Dörzbach et al. | 167/75 |
| 2,849,370 | 8/1958 | Petersen et al. | 167/75 |
| 3,060,093 | 10/1962 | Poulsen et al. | 167/75 |
| 3,868,358 | 2/1975 | Jackson | 260/112.7 |
| 5,028,587 | 7/1991 | Dörschug et al. | 514/3 |
| 5,149,777 | 9/1992 | Hansen et al. | 530/303 |
| 5,164,366 | 11/1992 | Balschmidt et al. | 514/3 |

FOREIGN PATENT DOCUMENTS

| | | |
|---|---|---|
| 889769 | 7/1958 | Denmark . |
| 0214826 | 3/1987 | European Pat. Off. . |
| 123703 | 3/1988 | Romania . |
| WO95/00550 | 1/1995 | WIPO . |

OTHER PUBLICATIONS

Howey, et al., *Diabetes*, 43, 396–402 (Mar. 1994).
*Diabetes*, 41, Suppl. 1, 192A (1992).
Brems, et al., *Protein Engineering*, 5:6, 519–525 (1992).
Heinemann, et al., *Diabetologia*, 33, 384–386 (1990).
Kirk–Othmer, *Encyclopedia of Chemical Technology* 13, 607–614 (1981).
Bruce H. Frank, Text and Slide copies of lecture given at the Conference on Insulin, Self Association and Conformational Studies on Human Proinsulin and Insulin Analogs, University of York, Aug. 29–Sep. 1, 1989.
Fullerton, et al., *Biochim. Biophys. Acta*, 214, 141–147 (1970).
*Diabetologia*, 30, 503A (1987).
Brange, et al., *Nature*, 333:16, 679–682 (Jun. 1988).
Brange, et al., *Diabetes Care*, 13:9, 923–954 (Sep. 1990).
Wollmer, et al., *Phenol–Promoted Structural Transformation of Insulin in Solution*, from the 2nd Assisi International Symposium on Advanced Models for the Therapy of Insulin–Dependent Diabetes, 903–911 (Apr. 1986).
Brange, *Galenics of Insulin: The Physico–chemical and Pharmaceutical Aspects of Insulin and Insulin Preparations*, Springer–Verlag Berlin Heidelberg, Germany (1987).
Simkin, et al., *Biochimica Et Biophysica Acta*, 200, 385–394 (1970).
Brems, et al., *Protein Engineering*, 5:6, 527–533 (1992).
Chen, et al., *Proc. Natl. Sci. Counc, ROC(A)*, 6:3, 185–189 (1982).
Galloway, et al., *Insulin Update*, 111–119 (1982).
Balschmidt, et al., *Acta Cryst*, 975–986 (1991).
Krayenbül, et al., *Crystalline Protamine Insulin* (60–73).
Brange, et al., *Structural Biology*, 1, 934–940 (1991).
Chance, et al. Serial No. 08/057201, Filed May 5, 1993.

Primary Examiner—Jill Warden
Assistant Examiner—Benet Prickril
Attorney, Agent, or Firm—Steven P. Caltrider; Gerald V. Dahling; David E. Boone

[57] ABSTRACT

The present invention discloses various parenteral pharmaceutical formulations, which comprise: a monomeric insulin analog, zinc, protamine, and phenolic derivative. The analog formulations provide a prolonged duration of action. A process for preparing insulin analog-protamine formulations is also described.

21 Claims, 1 Drawing Sheet

MONOMERIC INSULIN ANALOG FORMULATIONS

FIELD OF INVENTION

The present invention relates to monomeric analogs of human insulin. More specifically, the present invention relates to various parenteral formulations, which comprise a monomeric insulin analog, zinc, protamine, and a phenolic derivative. The formulations provide a prolonged duration of action. A process for preparing insulin analog-protamine formulations is also described.

BACKGROUND OF THE INVENTION

Since the introduction of insulin in the 1920's, continuous strides have been made to improve the treatment of diabetes mellitus. Major advances have been made in insulin purity and availability with the development of recombinant DNA technology. Various formulations with different time-actions have also been developed. Currently, there are generally seven commercially available insulin formulations: Regular insulin; semilente insulin, globin insulin, isophane insulin, insulin zinc suspension, protamine zinc insulin, and Ultralente insulin.

Despite the array of formulations available, subcutaneous injection therapy still falls short of providing a patient with convenient regulation and normalized glycemic control. Frequent excursions from normal glycemia levels over a patient's lifetime lead to hyper-or hypoglycemia, and long term complications including retinopathy, neuropathy, nephropathy, and micro- and macroangiopathy.

To help avoid extreme glycemic levels, diabetics often practice multiple injection therapy whereby insulin is administered with each meal. However, this therapy has not yet been optimized. The most rapid-acting insulin commercially available peaks too late after injection and lasts too long to optimally control glucose levels. Therefore, considerable effort has been devoted to create insulin formulations and insulin analog formulations that alter the kinetics of the subcutaneous absorption process.

Because all commercial pharmaceutical formulations of insulin contain insulin in the self-associated state and predominately in the hexamer form, it is believed that the rate-limiting step for the absorption of insulin from the subcutaneous injection depot to the bloodstream is the dissociation of the self-aggregated insulin hexamer. Recently, monomeric insulin analogs have been developed that are less prone to association to higher molecular weight forms than human insulin. This lack of self-association is due to modifications in the amino acid sequence of human insulin that decrease association by primarily disrupting the formation of dimers. See, e.g., Brems et al., *Protein Engineering*, 5:6, 527–533 (1992) and Brange et al., *Nature*, 333:679–682 (1988). Accordingly, monomeric insulin analogs possess a comparatively more rapid onset of activity while retaining the biological activity of native human insulin. These insulin analogs provide a rapid absorption to place injection time and peak action of insulin into closer proximity with postprandial glucose excursion associated in the response to a meal.

The physical properties and characteristics of monomeric analogs are not analogous to insulin. For example, Brems et al. disclose that various monomeric analogs have little, or no, Zn-induced association. Any association that is observed is to a multitude of higher molecular weight forms. This differs dramatically from insulin, which is almost exclusively in an ordered, hexamer conformation in the presence of zinc. Brange et al. *Diabetes Care* 13:923–954 (1990). The lack of association attributes to the fast acting characteristics of the analogs. Because the analogs have lower tendency to associate, it is quite surprising that a monomeric insulin analog can be formulated to provide an intermediate duration of action.

The present invention provides a monomeric insulin analog formulation that yields upon use an intermediate duration of action. The invention further provides a novel protamine crystal called insulin analog-NPD. The present invention also provides a mixture of insulin analog-NPD and soluble monomeric insulin analog. This mixture provides a rapid onset of action and an intermediate duration of action. Accordingly, the mixture possesses advantages over both insulin and the monomeric analog. The present invention further provides for a process for preparing uniform crystals of insulin analog-NPD.

SUMMARY OF THE INVENTION

This invention provides an insulin analog-protamine formulation, which comprises: a monomeric insulin analog, protamine, zinc, and a phenolic derivative.

The invention further provides a crystalline insulin analog-protamine complex. This complex has been defined as insulin analog-NPD. $Lys^{B28}Pro^{B29}$-human insulin-NPD comprises: a $Lys^{B28}Pro^{B29}$-human insulin, about 0.27 to about 0.32 mg protamine/100 U of insulin analog, about 0.35 to about 0.9% zinc by weight, and a phenolic derivative.

This invention additionally provides a process for preparing $Lys^{B28}Pro^{B29}$-human insulin-NPD, which comprises:

combining an aqueous solution of $Lys^{B28}Pro^{B29}$-human insulin in a hexamer association state, and a protamine solution at a temperature from about 8° to about 22° C.;

said aqueous solution comprising from about 0.35 to about 0.9% zinc by weight, $Lys^{B28}Pro^{B29}$-human insulin, and a phenolic derivative at a pH of about 7.1 to about 7.6;

said protamine solution comprising protamine at a pH of about 7.1 to about 7.6 such that the final concentration of protamine is about 0.27 to about 0.32 mg protamine/100 U of insulin analog.

The invention also provides formulations that are both rapid and intermediate acting. The formulations are mixtures of monomeric insulin analog and crystalline insulin analog-NPD, wherein the ratio by weight of the two components is about 1–99:99–1.

Finally, the invention provides a method of treating a patient suffering from diabetes mellitus, which comprises administering to said patient a pharmaceutical composition containing insulin analog-protamine crystals.

DETAILED DESCRIPTION AND PREFERRED EMBODIMENTS

Figure 1:
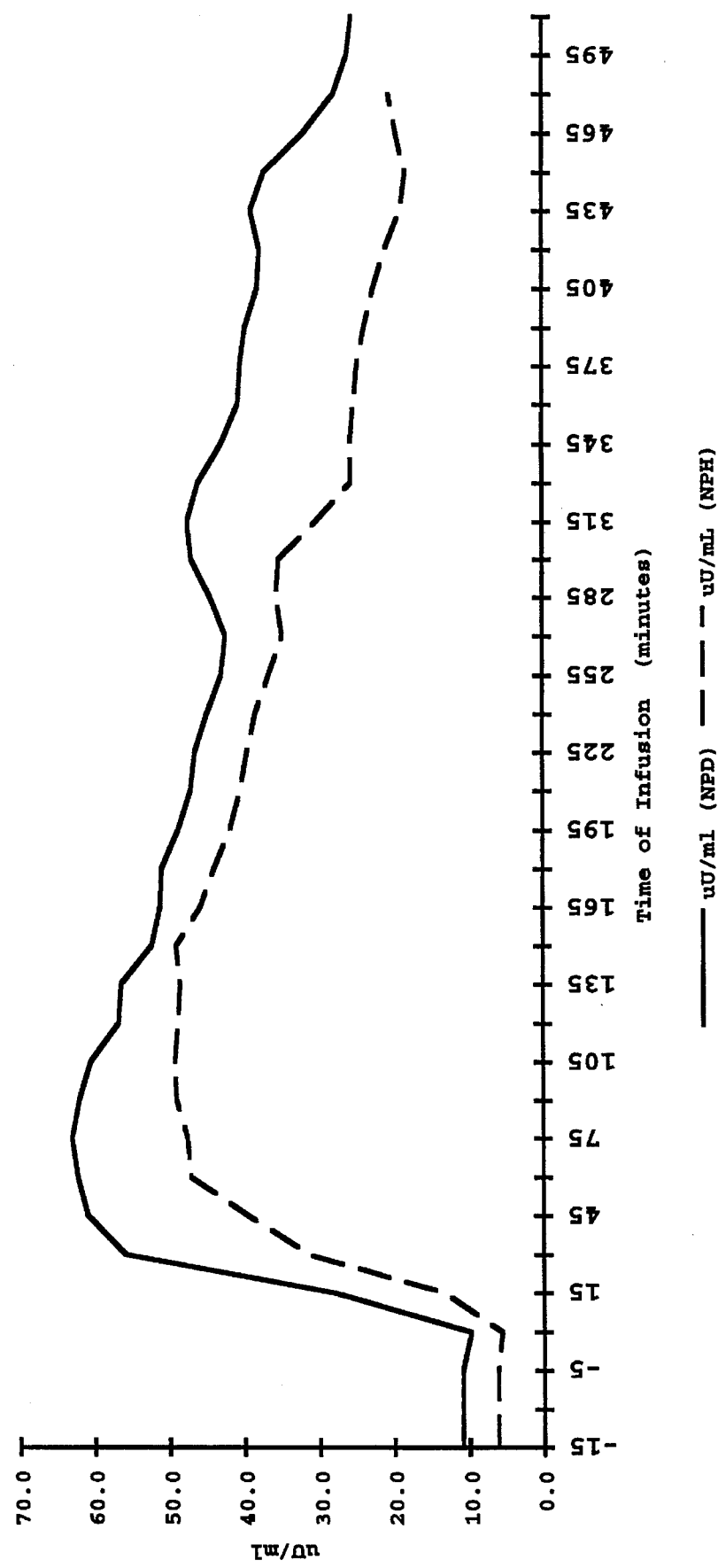
FIG. 1 is a graphical representation of the profile of action of $Lys^{B28}Pro^{B29}$-hI-NPD and human insulin-NPH. The graph is µU/ml versus the Time of Infusion. The figure demonstrates the advantages of the present invention.

As noted above, the invention provides various formulations of a monomeric insulin analog. The term "monomeric insulin analog" or "insulin analog" as used herein is a fast-acting insulin analog that is less prone to dimerization or self-association. Monomeric insulin analog is human insulin wherein Pro at postion B28 is substituted with Asp, Lys, Leu, Val, or Ala, and Lys at position B29 is Lysine or Proline; des(B28–B30); or des(B27). Monomeric insulin analogs are described in Chance et al., U.S. patent application Ser. No. 07/388,201, (EPO publication number 383 472), and Brange et al., EPO publication 214 826, and are herein incorporated by reference.

One skilled in the art would recognize that other modifications to the monomeric insulin analog are possible. These modifications are widely accepted in the art and include replacement of the histidine residue at position B10 with aspartic acid; replacement of the phenylalanine residue at position B1 with aspartic acid; replacement of the threonine residue at position B30 with alanine; replacement of the serine residue at position B9 with aspartic acid; deletion of amino acids at position B1 alone or in combination with a deletion at position B2; and deletion of threonine from position B30.

All amino acid abbreviations used in this disclosure are those accepted by the United States Patent & Trademark Office as set forth in 37 C.F.R. § 1.822(b) (2). Particularly preferred monomeric insulin analogs are $Lys^{B28}Pro^{B29}$-human insulin (B28 is Lys; B29 is Pro) and $Asp^{B28}$-human insulin (B28 is Asp).

The term "monomeric insulin analog-NPD" or "insulin analog-NPD" is a suspension of crystalline insulin analog and protamine in a formulation. NPD is Neutral Protamine formulation according to DeFelippis. The composition is prepared in accordance to the claimed process described herein. A related term "insulin analog NPD crystals," "crystalline insulin analog-NPD," or "$Lys^{B28}Pro^{B29}$-human insulin-protamine crystals" refer to the insulin analog-protamine crystals in the NPD formulation.

The term "treating," as used herein, describes the management and care of a patient for the purpose of combating the disease, condition, or disorder and includes the administration of a compound of present invention to prevent the onset of the symptoms or complications, alleviating the symptoms or complications, or eliminating the disease, condition, or disorder.

The term "isotonicity agent" refers to an agent that is physiologically tolerated and embarks a suitable tonicity to the formulation to prevent the net flow of water across the cell membrane. Compounds, such as glycerin, are commonly used for such purposes at known concentrations. The concentration of the isotonicity agent is in the range known in the art for insulin formulations.

The term "phenolic derivative" is m-cresol, phenol or preferably a mixture of m-cresol and phenol.

The term "free base basis" indicates the amount of protamine in the formulation. Free base basis corrects for the water and salt content of the protamine salts commercially available and commonly used in parenteral formulations. The preferred protamine, protamine sulfate, is approximately 80% protamine.

The term "IU" or "U" is international unit.

The term "isophane ratio" is the equilibrium amount of protamine necessary to complex with the analog as taught by Krayenbühl and Rosenberg, STENO MEMORIAL HOSPITAL REPORT (COPENHAGEN), 1:60 (1946). The isophane ratio is determined by titration in a manner well known in the art and described in Krayenbühl, et al.

The present invention provides an insulin analog-protamine formulation, which comprises: a monomeric insulin analog, protamine, zinc, and a phenolic derivative. The concentration of protamine is preferably about 0.2 to about 1.5 mg of protamine to 100 U of insulin analog on a free base basis. The concentration of zinc is from about 0.35 to about 0.9% on a weight basis. Preferably, the concentration of zinc is about 0.7%.

The phenolic derivative is m-cresol, phenol or a mixture of m-cresol and phenol. Preferably the phenolic derivative is m-cresol and phenol. The concentration of the phenolic derivative is known to one skilled in the art. The concentrations must be sufficient to maintain preservative effectiveness, i.e., retard microbial growth. In general, the concentration of phenolic is greater than about 2.5 mg/ml. The preferred concentration is about 3 mg/mL. The presence of a phenolic derivative is critical because it acts to complex the analog, protamine and zinc in addition to serving as a preservative.

Preferably, an isotonicity agent is added to the formulation. The preferred isotonicity agent is glycerin. The concentration of the isotonicity agent is preferably about 16 mg/mL.

The pH of the formulation may be buffered with a physiologically tolerated buffer, preferably a phosphate buffer, like dibasic sodium phosphate. Other physiologically tolerated buffers include TRIS, sodium acetate, or sodium citrate. The selection and concentration of buffer is known in the art. Preferably, the concentration is about 3.8 mg/mL.

The present invention further provides specific conditions under which the insulin analog-protamine exists as a stable crystal. Formulations of these crystals are defined as insulin analog-NPD. Insulin analog-NPD is a formulated suspension of insulin analog-NPD crystals and yields upon use an intermediate duration of action. The profile of activity of insulin analog-NPD is quite surprising in view of the lack of self-association of the monomeric analog.

The ability to form an intermediate acting formulation with a monomeric analog is demonstrated in FIG. I. FIG. 1 discloses a profile of action for $Lys^{B28}Pro^{B29}$-hI-NPD and human insulin-NPH. The NPD profile is similar to insulin-NPH. The duration of action for the NPD formulation and the insulin-NPH formulation are approximately equal. However, most significantly, the present formulation rises more rapidly and remains stable for a longer period than insulin-NPH. This difference is quite unexpected in view of the fast-acting profile of the monomeric analog.

A particularly preferred insulin analog-protamine formulation, $Lys^{B28}Pro^{B29}$-human insulin-NPD, comprises: $Lys^{B28}Pro^{B29}$-human insulin, about 0.27 to about 0.32 mg protamine/100 U of insulin analog, about 0.35 to about 0.9% zinc by weight, and a phenolic derivative. The concentration of protamine is preferably 0.3 mg/100 U on a free base basis.

The invention also provides the process for preparing $Lys^{B28}Pro^{B29}$-human insulin-protamine crystals, which comprises:

combining an aqueous solution of $Lys^{B28}Pro^{B29}$-human insulin in a hexamer association state, and a protamine solution at a temperature from about 8° to about 22° C.;

said aqueous solution comprising from about 0.35 to about 0.9% zinc by weight, $Lys^{B28}Pro^{B29}$-human insulin, and a phenolic derivative at a pH of about 7.1 to about 7.6;

said protamine solution comprising protamine at a pH of about 7.1 to about 7.6 such that the final concentration of protamine is about 0.27 to about 0.32 mg protamine/100 U of insulin analog.

At the time of invention it was known that monomeric insulin analogs have a lesser tendency to associate and form hexamers. The conditions necessary to cause the monomeric insulin analogs to associate with protamine to form crystals were previously unknown in the art. Previous studies relate to insulin. The teachings regarding the preparation of insulin-NPH (neutral protamine formulation according to Hagedorn) or isophane insulin formulations by Krayenbühl and Rosenberg, STENO MEMORIAL HOSPITAL REPORT (COPENHAGEN), 1:60 (1946) are not relevant in view of the distinct properties of the monomeric insulin analogs. In fact, the commercial process of producing Humulin-N™ (insulin-NPH), an acid-neutral process, does not produce crystalline insulin analog-NPD.

Most significantly, it has been found that the parameters in the present process—namely, the temperature of the crystallization and the formation of a hexamer complex of the insulin analog, zinc, and the phenolic derivative are critical limitations to the formation of stable, $Lys^{B28}Pro^{B29}$-hI-NPD crystals.

The temperature of the crystallization must be from about 8° C. to about 22° C., preferably from 13° C. to 17° C. If the temperature is outside of this range, a largely amorphous insulin analog-protamine formulation results.

It is also critical that the insulin analog be transformed to a hexamer state prior to the crystallization. The crystallization results in an amorphous product when the process is carried out with a monomeric association state. Crystals form without agitation in five to thirty-six hours hours. Good quality crystals are generally formed in 24 hours.

Soluble monomeric insulin analog is complexed to a hexamer association state by suspending solid monomeric analog in a diluent containing the phenolic derivative and adding zinc until the concentration is from about 0.35% to about 0.9% on a weight basis. Zinc is preferably added as a salt. Representative examples of zinc salts include zinc acetate, zinc bromide, zinc chloride, zinc fluoride, zinc iodide and zinc sulfate. The skilled artisan will recognize that there are many other zinc salts that also might be used in the process of the present invention. Preferably, zinc acetate or zinc chloride is used.

Dissolution of the insulin analog in the diluent may be aided by what is commonly known as an acid dissolution, In an acid dissolution, the pH is lowered to about 3.0 to 3.5 with a physiologically tolerated acid, preferably HCl, to increase solubility of the analog. Other physiologically tolerated acids include acetic acid, citric acids and phosphoric acid. The pH is then adjusted with a physiologically tolerated base, preferably NaOH to about 7.1 to 7.6 for the crystallization. Other physiologically tolerated bases include KOH and ammonium hydroxide.

Host significantly, the process of producing $Lys^{B28}Pro^{B29}$-hI-NPD complex is sensitive to the concentration of NaCl. If the concentration exceeds about 4 mg/mL, the insulin analog-NPD crystals become mixed with amorphous product. Accordingly, it is preferred that the monomeric analog is dissolved at neutral pH to avoid the formation of salt ions. Alternatively, the analog may be dissolved in the diluent at an acid pH prior to the addition of the buffer. This reduces the concentration of salts generated due to the pH adjustment. However, the order that the constituents are added is not critical to the formation of the hexamer or the amorphous formulation.

As previously disclosed, an isotonicity agent may be added to the formulations of the present invention. The addition of the isotonicity agent can be to the analog solution, to the protamine solution, or to the final insulin analog-NPD formulation. Likewise, the addition of the physiologically tolerated buffer may be added to the analog solution, to the protamine solution, or to the final insulin analog-NPD formulation. However, it is preferred that both the analog solution and the protamine solution contain the isotonicity agent and the buffer prior to combining the aqueous solution and the protamine. Because of the NaCl effects on the process for producing crystalline insulin-analog-NPD, glycerin is the preferred isotonicity agent.

The invention also provides insulin analog formulations, which comprise mixtures of insulin analog-NPD as a crystalline solid and soluble insulin analog. These mixtures are prepared in a range of about 1:99 to 99:1, by volume suspended insulin analog-NPD to soluble insulin analog. The soluble insulin analog is a monomeric insulin analog dissolved in an aqueous diluent comprising: zinc, a phenolic derivative, an isotonicity agent, and buffer. The concentrations described in the diluent are the same as previously disclosed herein. Preferably the ratio of insulin analog-NPD to soluble insulin analog is 25:75 to 75:25; and more preferably, 50:50. The mixtures are readily prepared by mixing the individual constituents.

The mixed formulations of the present invention are especially suitable for the treatment of diabetes mellitus because of the combination of a rapid onset of action and prolonged duration. These mixtures allow "fine control" by varying the amount of each individual constituent based on the needs, diet, and physical activity of the patient. The mixture of suspended insulin-analog-NPD and soluble insulin analog are also advantageous because they are homogeneous, i.e., any equilibrium exchange between the suspended crystals and soluble insulin analog is transparent.

The insulin analogs of the present invention can be prepared by any of a variety of recognized peptide synthesis techniques including classical (solution) methods, solid phase methods, semi synthetic methods, and more recent recombinant DNA methods. For example, Chance et al., U.S. patent application Ser. No. 07/388201, EPO publication number 383 472, and Brange et al., EPO 214 826, disclose the preparation of various monomeric analogs.

The following examples are provided merely to further illustrate the preparation of the insulin analogs and the invention. The scope of the invention is not construed as merely consisting of the following examples.

Example 1

Preparation of $Lys^{B28}Pro^{B29}$-hI-NPD

A solution of $Lys^{B28}Pro^{B29}$-human insulin ($Lys^{B28}Pro^{B29}$-hI) at 200 IU/mL (U200) concentration was prepared by dissolving zinc containing crystals of $Lys^{B28}Pro^{B29}$-hI in a preservative/buffer system containing: 1.6 mg/mL m-cresol, 0.73 mg/mL phenol (equivalent to 0.65 mg/mL phenol calculated as 89 %), 16 mg/mL glycerin, and 3.78 mg/mL of dibasic sodium phosphate buffer. The endogenous zinc level in the crystals was supplemented by adding an appropriate volume of an acidic ZnO solution (10 mg/mL) to achieve a final concentration of 0.025 mg/100 IU (0.7%). Dissolution of $Lys^{B28}Pro^{B29}$-hI was accomplished at ambient temperature by lowering the pH to about 3 with μL volumes of 5 M HCl. After the solution had clarified, the pH was readjusted to 7.5 with μL volumes of 5 M NaOH.

A protamine solution was prepared by dissolving enough solid protamine sulfate in the preservative/buffer solution to achieve a final concentration of 0.6 mg/100 IU calculated on a free base basis. The pH of this solution was adjusted to 7.5 and equilibrated at 15° C.

Both solutions were diluted to final concentration with water for injection and filtered. 5 mL aliquots of the $Lys^{B28}Pro^{B29}$-hI subsection were filled into separate clean glass vials, and the samples were incubated in a water bath at 15° C. After appropriate time for equilibration (15 minutes), precipitation was induced by rapidly adding 5 mL of the protamine solution to the $Lys^{B28}Pro^{B29}$-hI samples. The crystallization was allowed to proceed about 24 hours at 15° C.

Example 2

Preparation of $Lys^{B28}Pro^{B29}$-hI-NPD

The process is identical to Example 1, except that the dissolution of $Lys^{B28}Pro^{B29}$-hI occurs at neutral pH. The process was carried out such that the final pH was 7.4.

Example 3

Preparation of $Lys^{B28}Pro^{B29}$-hI-NPD

Insulin analog-NPD was prepared in a manner analogous to Example 1, but the acid dissolution of $Lys^{B28}Pro^{B29}$-hI was carried out in the presence of all excipients except the dibasic sodium phosphate buffer. Solid dibasic sodium phosphate is added after the insulin analog solution was returned to pH 7.4. The addition of dibasic sodium phosphate clarified the solution.

Example 4

Preparation of insulin analog-NPD mixture formulations

Mixtures of intermediate and rapid acting $Lys^{B28}Pro^{B29}$-hI formulations are prepared as follows. The intermediate acting, suspension preparation is prepared by the methods described in Example 3 and serves as the intermediate acting section for the mixture. A separate solution of $Lys^{B28}Pro^{B29}$-hI (100 IU) is prepared by dissolving zinc-containing $Lys^{B28}Pro^{B29}$-hI crystals at ambient temperature in the diluent described in Example 1. The endogenous zinc level of $Lys^{B28}Pro^{B29}$-hI in this solution is supplemented by the addition of acidic ZnO solution to match the level in the suspension section (i.e., 0.025 mg/100 IU (0.7%)). Water for injection is used to dilute the solution to final concentration after the pH is adjusted to 7.4 using 10% solutions of HCl and/or NaOH. This solution is the rapid acting section of the mixtures. The final mixture is prepared by combining appropriate volumes of the intermediate and rapid acting subsections to achieve the desired ratio. A 50/50 mixture is prepared by combining 1 part of the intermediate acting section with 1 part of the rapid acting section by volume.

Example 5

Effect of ionic strength on $Lys^{B28}Pro^{B29}$-hI protamine crystallization

The effect of ionic strength on the crystallization was evaluated by the addition of NaCl to the $Lys^{B28}Pro^{B29}$-hI section prior to mixing with protamine. NaCl was added so that the total concentration was 20, 30, and 40 mM (1.2, 1.8, and 2.3 mg/ml). The volume particle size displayed multimodal behaviour (additional peaks at small particle sizes), as the NaCl concentration was increased. The volume mean particle size decreased as NaCl concentration was increased indicating an increase in amorphous material. Results of particle size vs. NaCl concentration are as follows:

| [NaCl] | Volume Mean Particle Size (μm) |
|---|---|
| 13 mM | 3.9 |
| 20 mM | 3.5 |
| 30 mM | 3.3 |
| 40 mM | 3.2 |

The microscope analysis showed that all samples contained a mixture of amorphous and crystalline material. The sample containing 40 mM NaCl had mostly amorphous material and very few crystals.

Example 6

Comparative dynamics of $Lys^{B28}Pro^{B29}$-hI-NPD and human insulin-NPH

This study was carried out in a conscious dog model. Prior to the commencement of the study, three basal samples were taken. An infusion of somatostatin (0.3 μg/Kg-min.) was initiated. After a 10 minute interval, a subcutaneous injection of either NPD or NPH was administered. Frequent monitoring of plasma glucose was initiated and a variable glucose (20%) infusion was given so as to maintain near-normal glycemia. Samples were taken throughout and were analyzed for immunoreactive insulin (Linco antibody) and glucose. The results are illustrated in FIG. 1.

Example 7

Preparation of Asp(B28) Analog-Protamine Crystals

A subsection of Asp(B28)-hI at 200 IU/mL (U200) concentration was prepared by dissolving lyophilized bulk (95% purity) in a preservative/buffer system containing: 1.6 mg/mL m-cresol, 0.73 mg/mL phenol (equivalent to 0.65 mg/mL phenol calculated as 89%), 16 mg/mL glycerin, and 3.78 mg/mL dibasic sodium phosphate. Zinc was added to the system using an appropriate volume of an acidic ZnO solution (10 mg/mL) to obtain a final concentration of 0.025 mg/100 IU. Dissolution of Asp(B28) was achieved at ambient temperature at neutral pH. The final pH of the section was 7.4.

A crystallization was carried as described in Example 2. Final protamine concentrations of 0.3 mg/100 U, 0.35 mg/100 U, and 0.4 mg/100 U were investigated. Incubation temperatures included 5° C. (0.3 mg/100 U only), 15° C. and 22° C. After 24 hr. at these temperatures, samples were analyzed for crystal formation. Results as determined by microscopy illustrate a mixture of a few crystals and amorphous product.

Example 8

Preparation of Asp(B28) Analog. Protamine Crystals

The crystallization Asp(B28) Protamine was performed as described in Example 7, except that the protein was first dissolved in a buffer-free diluent. The addition of the acidic ZnO stock was sufficient to acidify the sample to pH 2.0–2.5. After the solution had clarified, the pH was readjusted to approximately pH 7 with μL volumes of 5N NaOH. Sodium phosphate, dibasic, was added using a concentrated stock solution at 47.25 mg/mL to achieve the final concentration of 3.78 mg/mL. The subsection was adjusted to pH 7.4 using μL quantities of HCl.

Crystallization was initiated by combining the Asp(B28) and protamine sections, as described in previous examples. Final protamine concentrations of 0.3 mg/100 U, 0.35 mg/100 U, and 0.4 mg/100 U were investigated. Incubation temperatures included 15° C. and 22° C. After 24 hr. at these temperatures, samples were analyzed for crystal formation. Results as determined by microscopy illustrate a mixture of a crystals and amorphous material.

Example 9

Preparation of Leu(B28)Pro(B29) Analog-Protamine Crystals

A subsection of Leu(B28)Pro(B29) (93% purity) at 200 IU/mL (U200) concentration was prepared as described in Example 8 using an acid dissolution of the bulk followed by pH adjustment with 5N NaOH to pH 7.4. Crystallization was as described above. Final protamine concentrations of 0.3 mg/100 U, 0.35 mg/100 U, and 0.4 mg/100 U were investigated. Incubation temperatures included 5° C., 15° C. and 22° C. After 24 hr. at these temperatures, all samples contain some crystals, but were primarily amorphous as determined by microscopy.

Example 10

Des(B27)hI-protamine crystals

A subsection of DesThr(B27) (97.37% purity) at 200 IU/mL (U200) concentration was prepared as described in Example 8 using an acid dissolution of the bulk followed by pH adjustment with 5N NaOH to pH 7.4. A crystallization was carried out as described in Example 8. Final protamine concentrations of 0.3 mg/100 U, 0.35 mg/100 U, and 0.4 mg/100 U were investigated. Incubation temperatures included 15° C. and 22° C. After 24 hr. at these temperatures, all samples were primarily amorphous as determined by microscopy. Qualitatively, crystals were observed.

Example 11

Des(B28-B30)hI-protamine

A subsection of Des(28–30) (96.3% purity) at 200 IU/mL (U200) concentration was prepared as described in Example 8 using an acid dissolution of the bulk followed by pH adjustment with 5N NaOH to pH 7.4. A crystallization was attempted using the neutral/neutral combination method of the protein and protamine sections as described above. Final protamine concentrations of 0.3 mg/100 U, 0.35 mg/100 U, and 0.4 mg/100 U were investigated. Incubation temperatures included 15° C. and 22° C. After 24 hr. at these temperatures, all samples were primarily amorphous as determined by microscopy. Qualitatively, crystals were observed. The crystals were well defined.

I claim:

1. A parenteral pharmaceutical insulin analog-protamine formulation, consisting essentially of: a monomeric insulin analog, protamine, zinc, and a phenolic derivative; wherein a monomeric insulin analog is human insulin wherein Pro at position B28 is substituted with Lys, Leu, Val, or Ala; Lys at position B29 is Lys or Pro; des(B28–B30)-human insulin; or des(B27)-human insulin.

2. A formulation of claim 1, wherein the concentration of protamine is about 0.2 to about 1.5 mg of protamine to 100 IU of insulin analog on a free base basis.

3. A formulation of claim 2, wherein the concentration of zinc is about 0.35 to about 0.9 percent by weight.

4. A formulation of claim 3, wherein the phenolic derivative is phenol and m-cresol.

5. A parenteral pharmaceutical formulation, which comprises: a monomeric insulin analog, about an isophane ratio of protamine, about 0.35 to about 0.9% zinc by weight, and a phenolic derivative; wherein a monomeric insulin analog is human insulin wherein Pro at position B28 is substituted with, Lys, Leu, Val, or Ala; Lys at position B29 is Lys or Pro; des(B28–B30)-human insulin or des(B27)-human insulin.

6. A parenteral pharmaceutical formulation, consisting essentially of: $Lys^{B28}Pro^{B29}$-human insulin, about 0.27 to about 0.32 mg protamine/100 U of insulin analog, about 0.35 to about 0.9% zinc by weight, and a phenolic derivative.

7. The parenteral pharmaceutical formulation of claim 6, wherein the $Lys^{B28}Pro^{B29}$-human insulin and protamine are crystalline.

8. The parenteral pharmaceutical formulation of claim 7, which further comprises an isotonicity agent.

9. The parenteral pharmaceutical formulation of claim 8, which further comprises a physiologically tolerated buffer.

10. The parenteral pharmaceutical formulation of claim 9, wherein the concentration of protamine is about 0.30 mg protamine/100 U of $Lys^{B28}Pro^{B29}$-human insulin.

11. The parenteral pharmaceutical formulation of claim 10, wherein the concentration of zinc is about 0.7%.

12. The parenteral pharmaceutical formulation of claim 5, wherein the insulin analog is $Leu^{B28}PRO^{B29}$-human insulin, des(B27)-human insulin, or des(B28-B30)-human insulin.

13. A process for preparing $Lys^{B28}Pro^{B29}$-human insulin-protamine crystals, which comprises:

combining an aqueous solution of $Lys^{B28}Pro^{B29}$-human insulin in a hexamer association state, and a protamine solution at a temperature from about 8° C. to about 17° C. to form crystals;

said aqueous solution comprising from about 0.35 to about 0.9% zinc by weight, $Lys^{B28}Pro^{B29}$-human insulin, and a phenolic derivative at a pH of about 7.1 to about 7.6;

said protamine solution comprising protamine at a pH of about 7.1 to about 7.6 such that the final concentration of protamine is about 0.27 to about 0.32 mg protamine/ 100 U of insulin analog provided that the process is carried out in less than 4 mg/mL sodium chloride.

14. The process of claim 13, wherein the temperature is from about 13° C. to about 17° C.

15. The process of claim 13, wherein the concentration of zinc is about 0.7%.

16. A parenteral pharmaceutical formulation, which comprises: a mixture of soluble monomeric insulin analog and insulin analog-NPD crystals, in an aqueous diluent wherein the ratio of the two insulin analogs is about 1:99–99:1 by volume insulin analog-NPD to soluble monomeric insulin analog, and wherein said soluble monomeric insulin analog is human insulin wherein Pro at position B28 is substituted with Lys, Leu, Val, or Ala; Lys at position B29 is Lys or Pro; des(B28–B 30)-human insulin or des(B27)-human insulin.

17. A parenteral pharmaceutical formulation of claim 16, wherein the mixture is $Lys^{B28}Pro^{B29}$-human insulin and $Lys^{B28}Pro^{B29}$-human insulin-protamine crystals.

18. The parenteral pharmaceutical formulation of claim 17, wherein the ratio is 75:25 to 25:75.

19. The parenteral pharmaceutical formulation of claim 18, wherein the ratio is 50:50.

20. A method of treating a patient suffering from diabetes mellitus, which comprises administering to said patient a pharmaceutical formulation of claim 1.

21. The method of claim 20, wherein the insulin analog is $Lys^{B28}Pro^{B29}$-human insulin.

* * * * *

UNITED STATES PATENT AND TRADEMARK OFFICE
CERTIFICATE OF CORRECTION

PATENT NO. : 5,461,031

DATED : Oct. 24, 1995

INVENTOR(S) : Michael R. DeFelippis

It is certified that error appears in the above-indentified patent and that said Letters Patent is hereby corrected as shown below:

Column 5, line 52,   "Host" should appear as --Most--

Column 10, line 23,   "PRO" should appear as --Pro--

Signed and Sealed this

Twenty-second Day of April, 1997

*Attest:*

BRUCE LEHMAN

*Attesting Officer*   Commissioner of Patents and Trademarks